United States Patent [19]

Kennewell et al.

[11] Patent Number: 4,472,401
[45] Date of Patent: Sep. 18, 1984

[54] PYRIMIDO-QUINOXALINES HAVING ANTIALLERGIC PROPERTIES

[75] Inventors: Peter D. Kennewell, Swindon; David P. Kay, Purton, both of England

[73] Assignee: Roussel Uclaf, Paris, France

[21] Appl. No.: 444,040

[22] Filed: Nov. 23, 1982

[30] Foreign Application Priority Data

Nov. 27, 1981 [GB] United Kingdom ............... 8135899

[51] Int. Cl.³ .................... A61K 31/505; C07D 487/04
[52] U.S. Cl. ..................................... 424/251; 544/250
[58] Field of Search .................. 544/250; 424/251

[56] References Cited

U.S. PATENT DOCUMENTS

| | | | |
|---|---|---|---|
| 4,127,720 | 11/1978 | Juby et al. ........................... | 544/252 |
| 4,145,419 | 3/1979 | Rowlands et al. ............... | 424/248.4 |
| 4,151,280 | 4/1979 | Rowlands et al. ............... | 424/250 |
| 4,207,318 | 6/1980 | Rowlands et al. ............... | 424/248.4 |
| 4,254,123 | 3/1981 | Ramm et al. ........................ | 424/250 |
| 4,279,912 | 7/1981 | Rowlands et al. ................ | 424/258 |
| 4,291,033 | 9/1981 | Barnes et al. ........................ | 424/250 |
| 4,333,934 | 6/1982 | Barnes et al. ........................ | 424/250 |

FOREIGN PATENT DOCUMENTS 1086666  10/1967  United Kingdom ............... 544/250

OTHER PUBLICATIONS

Hermecz, et al., J. Chem. Soc., Perkin Trans 1 (1977), pp. 789–795.

*Primary Examiner*—Donald G. Daus
*Assistant Examiner*—Diana G. Rivers
*Attorney, Agent, or Firm*—Charles A. Muserlian

[57] ABSTRACT

A compound selected from the group consisting of pyrimido quinoxalines of the formula

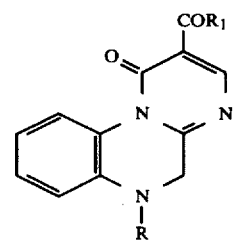

wherein $R_1$ represents an alkoxy radical of 1 to 5 carbon atoms and R is selected from the group consisting of hydrogen, alkyl of 1 to 5 carbon atoms, —$COR_4$, —CHO and

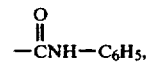

$R_4$ is selected from the group consisting of alkyl of 1 to 6 carbon atoms, cycloalkyl of 3 to 6 carbon atoms, alkoxy of 1 to 5 carbon atoms and phenyl optionally substituted with at least one member of the group consisting of halogen, —$NO_2$ and alkoxy of 1 to 3 carbon atoms and their non-toxic, pharmaceutically acceptable acid addition salts having antiallergic properties.

18 Claims, No Drawings

PYRIMIDO-QUINOXALINES HAVING ANTIALLERGIC PROPERTIES

STATE OF THE ART

Commonly assigned U.S. Pat. Nos. 4,254,123; 4,333,934 and to a lesser degree U.S. Pat. Nos. 4,145,419; 4,279,912; 4,151,280; 4,207,318 and 4,291,033 describe tricyclic compounds having antiallergic activity having a different chemical structure.

OBJECTS OF THE INVENTION

It is an object of the invention to provide the novel pyrimido-quinoxaline compounds of formula I and their non-toxic, pharmaceutically acceptable acid addition salts and their preparation.

It is another object of the invention to provide novel antiallergic compositions and a novel method of treating allergic conditions in warm-blooded animals.

These and other objects and advantages of the invention will become obvious from the following detailed description.

THE INVENTION

The novel compounds of the invention are selected from the group consisting of pyrimido-quinoxalines of the formula

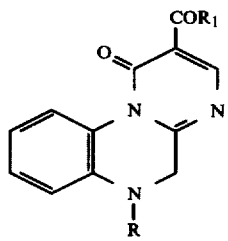

wherein $R_1$ represents an alkoxy radical of 1 to 5 carbon atoms and R is selected from the group consisting of hydrogen, alkyl of 1 to 5 carbon atoms, $-COR_4$, $-CHO$ and

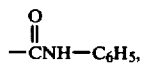

$R_4$ is selected from the group consisting of alkyl of 1 to 6 carbon atoms, cycloalkyl of 3 to 6 carbon atoms, alkoxy of 1 to 5 carbon atoms and phenyl optionally substituted with at least one member of the group consisting of halogen, $-NO_2$ and alkoxy of 1 to 3 carbon atoms and their non-toxic, pharmaceutically acceptable acid addition salts.

Examples of R are alkyl of 1 to 5 carbon atoms such as methyl, ethyl, propyl, isopropyl, butyl, isobutyl, tert.-butyl or pentyl; $-COR_4$ wherein $R_4$ is alkyl of 1 to 6 carbon atoms such as methyl, ethyl, propyl, isopropyl, butyl, isobutyl, tert.-butyl, pentyl or hexyl or $R_4$ is cycloalkyl of 3 to 6 carbon atoms such as cyclopropyl or cyclopentyl or $R_4$ is phenyl optionally substituted by one or more halogen atoms such as p-chlorophenyl, o-chlorophenyl, m-chlorophenyl or m,p-dichlorophenyl radical and $R_4$ and $R_1$ are alkoxy of 1 to 5 carbon atoms such as methoxy, ethoxy, propoxy, or butoxy.

Examples of suitable acids to form non-toxic, pharmaceutically acceptable acid addition salts are mineral or organic acids such as hydrochloric acid, hydrobromic acid, hydriodic acid, nitric acid, sulfuric acid, phosphoric acid, propionic acid, acetic acid, formic acid, benzoic acid, maleic acid, fumaric acid succinic acid, tartaric acid, citric acid, oxalic acid, glyoxylic acid or aspartic acid; alkanesulfonic acids e.g. methanesulfonic acid, or arylsulfonic acids e.g. benzenesulfonic acid.

Preferred compounds of the invention are those wherein $R_1$ is ethoxy, those wherein R is hydrogen, methyl, $-CO-R_4$ wherein $R_4$ is methyl, ethyl, isopropyl, cyclopropyl, cyclopentyl, phenyl, p-chlorophenyl or ethoxy or $-CHO$ or $-CO-NH-C_6H_5$. Particularly preferred compounds of the invention are ethyl 5,6-dihydro-1-oxo-1H-pyrimido [1,2-a] quinoxaline-2-carboxylate, ethyl 6-benzoyl-1-oxo-5,6-dihydro-1H-pyrimido [1,2,-a] quinoxaline-2-carboxylate and diethyl 5,6-dihydro 1-oxo-1H-pyrimido [1,2-a] quinoxaline-2,6-dicarboxylate and their non-toxic, pharmaceutically acceptable acid addition salts.

The compounds of formula I wherein R is hydrogen may be prepared by reduction of a compound of the formula

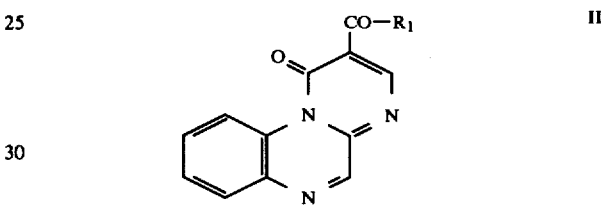

wherein $R_1$ is as defined above to obtain the corresponding compound of formula I. Reduction is preferably effected with hydrogen in the presence of a catalyst such as palladium and is conveniently effected in the presence of an inert organic solvent such as ethyl acetate and conveniently at ambient temperature.

The compounds of formula I wherein R is other than hydrogen may be prepared by reacting a compound of formula I wherein R is hydrogen with a reagent capable of introducing the desired R group other than hydrogen. When R is alkyl of 1 to 5 carbon atoms or $-COR_4$, the reagent is preferably a halide of the formula

$R^a-Hal$ wherein $R^a$ is selected from the group consisting of alkyl of 1 to 5 carbon atoms and $-COR_4$ and Hal is a halogen, preferably chlorine. The reaction is preferably effected under anhydrous conditions in the presence of an inert organic solvent such as dimethylformamide or methylene chloride, and preferably at ambient temperature. Alternatively, when it is desired to prepare a compound of formula I wherein R is methyl, the compound of formula I wherein R is hydrogen may be reacted with formaldehyde followed by reduction of the product thus obtained to obtain the desired 6-methyl compound of formula I.

The compounds of formula I wherein R is $-CHO$ may be obtained by reaction of the compound of formula I wherein R is hydrogen with formic acid and the reaction is preferably effected in the presence of a condensation agent such as carbonyldiimidazole and conveniently at ambient temperature.

The compounds of formula I wherein R is $-CO-NH-C_6H_5$ are preferably obtained by reaction of the compound of formula I wherein R is hydrogen with phenyl isocyanate and the reaction is preferably effected under anhydrous conditions in the presence of an inert organic solvent such as toluene and preferably at the reflux temperature of the reaction mixture.

The compounds of formula I may be converted into their acid addition salts by reaction with an acid, preferably in substantially stoichiometric amounts.

The compound of formula II wherein $R_1$ represents an ethoxy radical, useful as a starting material, is described by Hermecz et al in J. Chem. Soc., Perkin I, p. 789 (1977). The other compounds of formula II wherein $R_1$ is methoxy or alkoxy of 3 to 5 carbon atoms may be prepared by an analogous method.

The novel antiallergic compositions of the invention are comprised of an antiallergically effective amount of at least one compound of formula I and its non-toxic, pharmaceutically acceptable acid addition salts and an inert pharmaceutical carrier or excipient. The compositions may be in the form of tablets, dragees, gelatin capsules, granules, suppositories, syrups, aerosol, creams, ointments and injectable solutions and suspensions.

Examples of suitable excipients are talc, arabic gum, lactose, starch, magnesium stearate, cocoa butter, aqueous or non-aqueous vehicles, fatty substances of animal or vegetable origin, paraffin derivatives, glycols, various wetting dispersing or emulsifying agents and/or preservatives.

Advantageously, the compositions may be formulated as dosage units with each unit adapted to supply a fixed dose of active ingredient. Suitable dosage units for adults contain from 0.1 to 1000 mg, preferably from 1 to 100 mg of active ingredient and the oral daily dosage, which may be varied depending upon the compound used, the subject treated and the complaint concerned, may, for example, be from 1 to 1000 mg per day in adults.

The compositions due to their antiallergic properties are useful for the treatment of allergic asthma and asthmatic bronchitis of an allergic origin.

The novel method of the invention for treating allergic conditions in warm-blooded animals, including humans, comprises administering to warm-blooded animals an antiallergically effective amount of at least one compound of formula I and its non-toxic, pharmaceutically acceptable acid addition salts. The compounds may be administered orally, rectally, parenterally or topically and the usual daily dose is 0.015 to 15 mg/kg depending on the compound, the method of administration and the condition treated.

In the following examples there are described several preferred embodiments to illustrate the invention. However, it should be understood that the invention is not intended to be limited to the specific embodiments.

EXAMPLE 1

Ethyl 5,6-dihydro-1-oxo-1H-pyrimido [1,2-a] quinoxaline-2-carboxylate 5.0 g of ethyl 1-oxo-1H-pyrimido [1,2-a] quinoxaline-2-carboxylate [Hermecz et al., J. Chem. Soc. Perkin I, 789 (1977)] were dissolved in 400 ml of ethyl acetate and 1.0 ml of HCl was added thereto followed by 300 mg of 5% Pd-C. The mixture obtained was hydrogenated for 5 hours at room temperature and atmospheric pressure. On completion of the reaction, the solution was made alkaline with $NaHCO_3$ solution addition and filtered over celite. The organic phase was dried over $MgSO_4$ and evaporated to dryness under nitrogen at 35° C. to obtain 4.2 g (83% yield) of ethyl 5,6-dihydro-1-oxo-1H-pyrimido [1,2-a] quinoxaline-2-carboxylate melting at ≃170° C.

EXAMPLE 2

Diethyl 5,6-dihydro-1-oxo-1H-pyrimido [1,2-a] quinoxaline-2,6-dicarboxylate 4 ml of dry dimethylformamide were saturated with nitrogen for 10 minutes before 150 mg of ethyl chloroformate and 280 mg of ethyl 5,6-dihydro-1-oxo-1H-pyrimido [1,2-a] quinoxaline-2-carboxylate were added thereto. The solution obtained was left at room temperature overnight and then was poured into water. The mixture was extracted with ethyl acetate and the organic phase was dried over $MgSO_4$ and evaporated to dryness. The residue was chromatographed over silica gel and eluted with ethyl acetate to obtain 140 mg (41% yield) of diethyl 5,6-dihydro-1-oxo-1H-pyrimido [1,2-a] quinoxaline-2,6-dicarboxylate melting at 140°-2° C.

EXAMPLE 3

Ethyl 6-acetyl-5,6-dihydro-1-oxo-1H-pyrimido [1,2-a] quinoxaline-2-carboxylate

A mixture of 0.65 g of acetyl chloride and 1.5 g of sodium carbonate in 70 ml of dry methylene chloride was stirred under a nitrogen atmosphere while 1.5 g of ethyl 5,6-dihydro-1-oxo-1H-pyrimido [1,2,-a] quinoxaline-2-carboxylate were added thereto. The mixture was stirred for 4 hours and the solution was washed with water, dried over $MgSO_4$ and evaporated to dryness to obtain 1.45 g (84% yield) of ethyl 6-acetyl-5,6-dihydro-1-oxo-1H-pyrimido [1,2-a] quinoxaline-2-carboxylate melting at 152°-5° C.

EXAMPLES 4 TO 12

Using the procedure of Example 3 but starting from the corresponding chloride Cl—R in which R has the definition indicated in Table II, the compounds of Examples 4 to 12 were prepared.

TABLE II

| Ex | $R_1$ | R | Melting point °C. | Formula | Analysis Calculated C | H | N | Analysis Found C | H | N |
|---|---|---|---|---|---|---|---|---|---|---|
| 1 | $OC_2H_5$ | H | 170 (d) | $C_{14}H_{13}N_3O_3$ | 61.99 | 4.83 | 15.49 | 62.17 | 4.85 | 15.38 |
| 2 | $OC_2H_5$ | $CO_2Et$ | 140-2° | $C_{17}H_{17}N_3O_5$ | 59.47 | 4.99 | 12.24 | 59.51 | 5.03 | 11.97 |
| 3 | $OC_2H_5$ | $COCH_3$ | 152-5° | $C_{16}H_{15}N_3O_4$ | 61.34 | 4.83 | 13.41 | 61.08 | 4.83 | 13.31 |
| 4 | $OC_2H_5$ | $COCHMe_2$ | 123-4° | $C_{18}H_{19}N_3O_4$ | 63.33 | 5.61 | 12.31 | 63.46 | 5.68 | 12.21 |
| 5 | $OC_2H_5$ |  | 184-6° | $C_{18}H_{17}N_3O_4$ | 63.71 | 5.05 | 12.38 | 63.48 | 5.09 | 12.19 |
| 6 | $OC_2H_5$ | COPh | 168-70° | $C_{21}H_{17}N_3O_4$ | 67.19 | 4.56 | 11.19 | 66.90 | 4.59 | 11.11 |
| 7 | $OC_2H_5$ | COEt | 182-4° | $C_{17}H_{17}N_3O_4$ | 62.38 | 5.23 | 12.84 | 62.14 | 5.22 | 12.66 |

TABLE II-continued

| Ex | R₁ | R | Melting point °C. | Formula | Analysis Calculated C | H | N | Analysis Found C | H | N |
|---|---|---|---|---|---|---|---|---|---|---|
| 8 | OC₂H₅ | CO—⟨cyclopentyl⟩ | 92–5° | C₂₀H₂₁N₃O₄ | 65.38 | 5.76 | 11.44 | 65.08 | 5.86 | 11.18 |
| 9 | OC₂H₅ | CO—C₆H₄—Cl | 140–2° | | | | | | | |
| 10 | OC₂H₅ | CO—C₆H₄—OCH₃ | 105–7° | | | | | | | |
| 11 | OC₂H₅ | CO—C₆H₃(Cl)(Cl) | 120–2° | C₂₁H₁₅Cl₂N₃O₄ | 56.77 | 3.40 | 9.46 | 56.58 | 3.41 | 9.46 |
| 12 | OC₂H₅ | CO—C₆H₄—NO₂ | 134–5° | | | | | | | |
| 13 | OC₂H₅ | CHO | 172–4° | C₁₅H₁₃N₃O₄ | 60.26 | 4.38 | 14.04 | 60.31 | 4.44 | 13.91 |
| 14 | OC₂H₅ | CONHPh | 188–90° | C₂₁H₁₈N₄O₄ | 64.61 | 4.65 | 14.35 | 64.66 | 4.72 | 14.24 |
| 15 | OC₂H₅ | CH₃ | 111–4° | C₁₅H₁₅N₃O₃ | 63.15 | 5.30 | 14.73 | 62.75 | 5.35 | 14.53 |

EXAMPLE 13

Ethyl 5,6-dihydro-6-formyl-1-oxo-1H-pyrimido [1,2-a]quinoxaline-2-carboxylate

A solution of 700 mg of formic acid (98%) in 70 ml of CH₂Cl₂ was stirred at room temperature under nitrogen while 100 mg of carbonyldiimidazole were added thereto. After 30, minutes 1.5 g of ethyl 5,6-dihydro-1-oxo-1H-pyrimido [1,2-a] quinoxaline-2-carboxylate were added thereto and the mixture was stirred for another 6 hours. Then, the solution was poured into an aqueous NaHCO₃ solution and extracted with ethyl acetate. The organic layer was dried over MgSO₄, decolorized with charcoal and evaporated to dryness. The residue was crystallized from ethyl acetate to obtain 1.1 g (67% yield) of ethyl 5,6-dihydro-6-formyl-1-oxo-1H-pyrimido [1,2-a] quinoxaline-2-carboxylate melting at 172°–4° C.

EXAMPLE 14

Ethyl 5,6-dihydro-1-oxo-6-phenylcarbamoyl-1H-pyrimido [1,2-a] quinoxaline-2-carboxylate A mixture of 1.5 g of ethyl 5,6-dihydro-1-oxo-1H-pyrimido [1,2-a] quinoxaline-2-carboxylate and 0.8 ml of phenyl isocyanate in 70 ml of dry toluene was stirred and refluxed under nitrogen overnight, then cooled and filtered to obtain 1.47 (68% yield) of ethyl 5,6-dihydro-1-oxo-6-phenylcarbamoyl-1H-pyrimido [1,2-a] quinoxaline-2-carboxylate melting at 188°–90° C.

EXAMPLE 15

Ethyl 5,6-dihydro-6-methyl-1-oxo-1H-pyrimido [1,2-a] quinoxaline-2-carboxylate

A mixture of 1.5 g of ethyl 5,6-dihydro-1-oxo-1H-pyrimido [1,2-a] quinoxaline-2-carboxylate in 200 ml of ethyl alcohol and 0.5 g of concentrated hydrochloric acid was treated with 5.0 ml of 37% aqueous formaldehyde solution and 0.20 g of 5% Pd-C. The mixture was stirred under hydrogen at atmospheric pressure for 4 hours absorbing 110 ml of hydrogen and the mixture was filtered over celite. The filtrate was concentrated under reduced pressure and made alkaline by addition of a solution of 0.06 g of sodium bicarbonate in 60 ml of water and was extracted with ethyl acetate. The organic extracts were dried over MgSO₄ and evaporated to obtain 1.5 g of an orange solid. H.P.L.C. over silica gel and elution with 1% methanol/dichloromethane gave fractions 2 & 3 containing 0.8 g (51% yield) of pure ethyl 5,6-dihydro-6-methyl-1-oxo-1H-pyrimido [1,2-a] quinoxaline-2-carboxylate in the form of bright yellow crystals melting at 111°–4° C.

EXAMPLE 16

Tablets were prepared containing 15 mg of the Product of Example 1 and sufficient excipient for one tablet weighing 100 mg. The excipient was made of lactose, starch, talc and magnesium stearate.

EXAMPLE 17

A dosed aerosol was prepared delivering per dose: 2 mg of product of Example 1, 0.15 mg of emulsifier and 50 mg of propellant.

PHARMACOLOGICAL DATA

Passive cutaneous anaphylaxis in the rat (PCR)

Passive cataneous anaphylaxis in the rat was carried out in male Wistar rats weighing 180-200 g sensitized by intradermal injection into four sites on shaved backs so as to produce a passive cutaneous reaction mediated by Ig G antibodies (a 4 hour sensitization following injection of antiserum heated at 56° C. for one hour). Antigen challenge was carried out in the same way; 1 mg of ovalbumen together with 0.5 ml of 1% Evans blue dye solution was injected intravenously and 30 minutes later, the animals were killed and the severity and area of each blue spot was scored when viewed from the reverse side of the skin. The inhibition observed following oral administration of the tested compounds is given in Table I.

TABLE I

| Product of EXAMPLE | 0.1 mg/kg | % inhibition of Ig G PCR | |
|---|---|---|---|
| | | 1 mg/kg | 10 mg/kg |
| 1 | | 23.0 | 51.0 |
| 2 | | 31.0 | 34.9 |
| 3 | | 18.5 | 33.3 |
| 4 | 4.1 | 16.0 | 8.9 |
| 5 | | 23.0 | 33.3 |
| 6 | | 23.0 | 43.0 |
| 7 | | 8.2 | 5.8 |
| 8 | | 5.4 | 14.8 |
| 13 | 0.6 | 4.1 | 12.4 |
| 14 | | 17.6 | 15.2 |
| 15 | 7.7 | 7.7 | 30.2 |

Various modifications of the products and method of the invention may be made without departing from the spirit or scope thereof and it is to be understood that the invention is intended to be limited only as defined in the appended claims.

What we claim is:

1. A compound selected from the group consisting of pyrimido quinoxalines of the formula

[Chemical structure]

wherein $R_1$ represents an alkoxy radical of 1 to 5 carbon atoms and R is selected from the group consisting of hydrogen, alkyl of 1 to 5 carbon atoms, —$COR_A$, —CHO and —CNH—$C_6H_5$, $R_A$ is selected from the group consisting of alkyl of 1 to 6 carbon atoms, cycloalkyl of 3 to 6 carbon atoms, alkoxy of 1 to 5 carbon atoms and phenyl optionally substituted with at least one member of the group consisting of halogen, —$NO_2$ and alkoxy of 1 to 3 carbon atoms and their non-toxic, pharmaceutically acceptable acid addition salts.

2. A compound of claim 1 wherein $R_1$ is —$OCH_2$—$CH_3$.

3. A compound of claim 1 wherein R is selected from the group consisting of hydrogen, methyl, —CHO, —CONH—$C_6H_5$ and —$COR_A$ and $R_A$ is selected from the group consisting of methyl, ethyl, isopropyl, cyclopropyl, cyclopentyl, phenyl, p-chlorophenyl and ethoxy.

4. A compound of claim 1 selected from the group consisting of ethyl 5,6-dihydro-1-oxo-1H-pyrimido [1,2-a] quinoxalin-2-carboxylate and its non-toxic, pharmaceutically acceptable acid addition salts.

5. A compound of claim 1 selected from the group consisting of ethyl 6-benzoyl-5,6-dihydro-1-oxo-1H-pyrimido [1,2-a] quinoxalin-2-carboxylate and its non-toxic, pharmaceutically acceptable acid addition salts.

6. A compound of claim 1 selected from the group consisting of diethyl 5,6-dihydro-1-oxo-1H-pyrimido [1,2-a] quinoxalin-2,6-dicarboxylate and its non-toxic, pharmaceutically acceptable acid addition salts.

7. An antiallergic composition comprising an antiallergically effective amount of at least one compound of claim 1 and an excipient.

8. A composition of claim 7 wherein in the compound $R_1$ is —$OCH_2$—$CH_3$.

9. A composition of claim 7 wherein in the compound R is selected from the group consisting of hydrogen, methyl, —CHO, —CONH—$C_6H_5$ and —$COR_A$ and $R_A$ is selected from the group consisting of methyl, ethyl, isopropyl, cyclopropyl, cyclopentyl, phenyl, p-chlorophenyl and ethoxy.

10. A composition of claim 7 wherein the compound is selected from the group consisting of ethyl 5,6-dihydro-1-oxo-1H-pyrimido [1,2-a] quinoxalin-2-carboxylate and its non-toxic, pharmaceutically acceptable acid addition salts.

11. A composition of claim 7 wherein the compound is selected from the group consisting of ethyl 6-benzoyl5,6-dihydro-1-oxo-1H-pyrimido [1,2-a] quinoxalin-2-carboxylate and its non-toxic, pharmaceutically acceptable acid addition salts.

12. A composition of claim 7 wherein the compound is selected from the group consisting of diethyl 5,6-dihydro-1-oxo-1H-pyrimido [1,2-a] quinoxalin-2,6-dicarboxylate and its non-toxic, pharmaceutically acceptable acid addition salts.

13. A method of treating allergic conditions in warm-blooded animals comprising administering to warm-blooded animals an antiallergically effective amount of at least one compound of claim 1.

14. A method of claim 13 wherein in the compound $R_1$ is —$OCH_2$—$CH_3$.

15. A method of claim 13 wherein in the compound R is selected from the group consisting of hydrogen, methyl, —CHO, —CONH—$C_6H_5$ and —$COR_A$ and $R_A$ is selected from the group consisting of methyl, ethyl, isopropyl, cyclopropyl, cyclopentyl, phenyl, p-chlorophenyl and ethoxy.

16. A method of claim 13 wherein the compound is selected from the group consisting of ethyl 5,6-dihydro-1-oxo-1H-pyrimido [1,2-a] quinoxalin-2-carboxylate and its non-toxic, pharmaceutically acceptable acid addition salts.

17. A method of claim 13 wherein the compound is selected from the group consisting of ethyl 6-benzoyl 5,6-dihydro-1-oxo-1H-pyrimido [1,2-a] quinoxalin-2-carboxylate and its non-toxic, pharmaceutically acceptable acid addition salts.

18. A method of claim 13 wherein the compound is selected from the group consisting of diethyl 5,6-dihydro-1-oxo-1H-pyrimido [1,2-a] quinoxalin-2,6-dicarboxylate and its non-toxic, pharmaceutically acceptable acid addition salts.

* * * * *